(12) United States Patent
Kohl et al.

(10) Patent No.: US 7,470,791 B2
(45) Date of Patent: Dec. 30, 2008

(54) PROCESS FOR THE PREPARATION OF ROFLUMILAST

(75) Inventors: Bernhard Kohl, Constance (DE); Bernd Mueller, Constance (DE); Walter Palosch, Rielasingen (DE)

(73) Assignee: Nycomed GmbH, Konstanz (DE)

( * ) Notice: Subject to any disclaimer, the term of this patent is extended or adjusted under 35 U.S.C. 154(b) by 589 days.

(21) Appl. No.: 10/531,720

(22) PCT Filed: Mar. 8, 2004

(86) PCT No.: PCT/EP2004/050272

§ 371 (c)(1),
(2), (4) Date: Apr. 18, 2005

(87) PCT Pub. No.: WO2004/080967

PCT Pub. Date: Sep. 23, 2004

(65) Prior Publication Data

US 2006/0004061 A1 Jan. 5, 2006

(30) Foreign Application Priority Data

Mar. 10, 2003 (EP) .................................. 03005245

(51) Int. Cl.
*C07D 213/75* (2006.01)
(52) U.S. Cl. ..................................................... 546/309
(58) Field of Classification Search ........................ None
See application file for complete search history.

(56) References Cited

U.S. PATENT DOCUMENTS

| 5,340,827 | A | 8/1994 | Beeley et al. |
| 5,698,711 | A | 12/1997 | Palfreyman |
| 5,712,298 | A | 1/1998 | Amschler |
| 6,255,326 | B1 | 7/2001 | Ashton et al. |
| 6,448,274 | B2 | 9/2002 | Friesen et al. |
| 6,822,114 | B1 | 11/2004 | Williams et al. |

FOREIGN PATENT DOCUMENTS

| WO | 93/25517 | A1 | 12/1993 |
| WO | 94/02465 | A1 | 2/1994 |
| WO | 95/01338 | A1 | 1/1995 |
| WO | 01/90076 | A1 | 11/2001 |
| WO | 03/070279 | A1 | 8/2003 |
| WO | 03/099334 | A1 | 12/2003 |
| WO | 2004/033430 | A2 | 4/2004 |
| WO | 2005/026095 | A1 | 3/2005 |

OTHER PUBLICATIONS

Cook, D. C., et al., "Process Development Of The PDE IV Inhibitor 3-(Cyclopentyloxy)-*N*-(3,5-dichloropyrid-4-yl)-4-methoxybenzamide", *Organic Process Research & Development*, vol. 2, pp. 157-168, (1998).
Ried, P., "Roflumilast", *Current Opinion In Investigational Drugs*, vol. 3, No. 8, pp. 1165-1170, (2002).

*Primary Examiner*—Zinna N Davis
(74) *Attorney, Agent, or Firm*—The Nath Law Group; Joshua B. Goldberg; Sheldon M. McGee

(57) ABSTRACT

The invention relates to novel processes for the preparation of high-purity roflumilast.

162 Claims, No Drawings

PROCESS FOR THE PREPARATION OF ROFLUMILAST

This application is a 371 of PCT/EP04/50272 filed Mar. 10, 2003.

TECHNICAL FIELD

The present invention relates to a novel, improved process for the preparation of N-(3,5-dichloropyrid-4-yl)-3-cyclopropylmethoxy-4-difluoromethoxybenzamide (INN: roflumilast).

PRIOR ART

The international patent application WO 95/01338 describes the preparation of dialkoxy-substituted benzamides, including roflumilast, and the use thereof as PDE4 inhibitors. The international applications WO 94/02465 and WO 93/25517 also describe the preparation of dialkoxy-substituted benzamides. In the International patent application WO 03/070279 oral dosage forms comprising roflumilast are described. In the international patent application WO 03/099334 topically applicable pharmaceutical preparations comprising roflumilast are described. Organic Process Research & Development 2, 157-168 (1998) discloses improved processes for the preparation of 3-(cyclopentyloxy)-N-(3,5-dichloropyrid-4-yl)-4-methoxybenzamide (INN: piclamilast).

In the international applications WO 94/02465 and WO 93/125517, the dialkoxy-substituted benzamides are obtained by reacting activated benzoic acid derivatives of the general formula

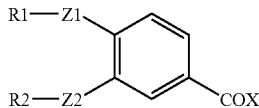

with amines of the general formula R3NH$_2$. Activated benzoic acid derivatives mentioned are acid halides, especially acid chlorides or else anhydrides. The reaction may take place in the presence of a base, e.g. of an organic base such as, for example, triethylamine, in the presence of a cyclic base such as, for example, N-methylmorpholine or pyridine or else in the presence of an alkali metal hydride such as, for example, sodium hydride, in an inert solvent such as, for example, tetrahydrofuran, dimethylformamide or dichloromethane.

3-(Cyclopentyloxy)-N-(3,5-dichloropyrid-4-yl)-4-methoxybenzamide (INN: piclamilast) is obtained in WO 93/25517 by reacting 3-cyclopentyl-4-methoxybenzoic acid, which has been deprotonated with N-methylmorpholine, with 4-amino-3,5-dichloropyridine in tetrahydrofuran. In WO 94/02465, 3-(cyclopentyloxy)-N-(3,5-dichloropyrid-4-yl)-4-methoxybenzamide (INN: piclamilast) is prepared by mixing together and subsequently melting 4-amino-3,5-dichloropyridine and 3-cyclopentyloxy-4-methoxybenzoyl chloride.

In the process for preparing roflumilast described in WO 95/01338, a solution of 0.0275 mol of 3-cyclopropylmethoxy-4-difluoromethoxybenzoyl chloride in tetrahydrofuran is added dropwise to a suspension of 0.03 mol of 4-amino-3,5-dichloropyridine and 0.066 mol of NaH (in mineral oil) in tetrahydrofuran at 15-20° C.

In the improved process described in Organic Process Research & Development 2, 157-168 (1998) for preparing 3-(cyclopentyloxy)-N-(3,5-dichloropyrid-4-yl)-4-methoxybenzamide (INN: piclamilast), firstly 0.218 mol of KOtBu is added to 0.22 mol of 4-amino-3,5-dichloropyridine at 90° C., and then a solution of 0.2 mol of 3-cyclopentyloxy-4-methoxybenzoyl chloride is added. The mixture is boiled under reflux for some time, cooled to 90° C. again and then a further 0.218 mol of KOtBu is added. This is followed by boiling under reflux again, before the reaction mixture is worked up by methods known to the skilled person.

None of the processes described in the international applications WO 93/25517 and WO 94/02465 for preparing piclamilast, nor the process described in WO 95/01338 for preparing roflumilast, appear to be suitable for the industrial preparation of roflumilast of high purity.

Although the improved process described in Organic Process Research & Development 2, 157-168 (1998) for preparing 3-(cyclopentyloxy)-N-(3,5-dichloropyrid-4-yl)-4-methoxybenzamide (INN: piclamilast) has already been optimized for feasibility on the industrial scale, when applied analogously to roflumilast it leads to the formation of more than 3% by weight of the by-product N-(3,5-dichloropyrld-4-yl)-3-cyclopropylmethoxy-4-hydroxybenzamide, which cannot be reduced even by multiple recrystallization.

DESCRIPTION OF THE INVENTION

It has now been found, surprisingly, that the formation of by-products, especially of the abovementioned by-product, can be very substantially averted when an activated derivative of 3-cyclopropylmethoxy-4-difluoromethoxybenzoic acid is reacted with an excess of the anion of 4-amino-3,5-dichloropyridine.

A first aspect of the invention is therefore a process for the preparation of roflumilast by reacting the anion of 4-amino-3,5-dichloropyridine (1)

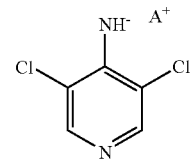

with an activated derivative of 3-cyclopropylmethoxy-4-difluoromethoxybenzoic acid (2),

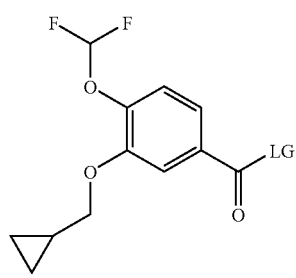

characterized in that the molar ratio of the employed anion of 4-amino-3,5-dichloropyridine to the activated derivative of 3-cyclopropylmethoxy-4-difluoromethoxybenzoic acid is at least 1.5 and at most 3, preferably at least 1.8 and at most 2.7, particularly preferably at least 2 and at most 2.5 and very particularly preferably 2.2.

$A^+$ in the formula 1 is a cation; $A^+$ is, for example, an alkali metal cation, preferably the potassium cation. LG in formula 2 is a suitable leaving group, preferably a chlorine atom, a bromine atom or a radical of the formula OC(O)-1-4C-alkyl. LG is particularly preferably a chlorine atom.

1-4C-alkyl in the formula OC(O)-1-4C-alkyl is a straight-chain or branched alkyl radical having 1 to 4 carbon atoms. Examples which may be mentioned are the butyl, isobutyl, sec-butyl, tert-butyl, propyl, isopropyl, ethyl and methyl radicals.

Reaction of the anion of 4-amino-3,5-dichloropyridine (1) with an activated derivative of 3-cyclopropylmethoxy-4-difluoromethoxybenzoic acid (2) can be carried out in all conventional inert solvents such as, for example, dichloromethane, toluene, xylene, dimethylformamide or N-methylpyrrolidone. The use of dimethylformamide or N-methylpyrrolidone is preferred. The use of dimethylformamide is very particularly preferred.

A further aspect of the invention is therefore one of the processes described above for preparing roflumilast, characterized in that reaction of the anion of 4-amino-3,5-dichloro-pyridine (1) with an activated derivative of 3-cyclopropyl-methoxy-4-difluoromethoxybenzoic acid (2) is carried out in a solvent selected from the group of dichloromethane, toluene, xylene, dimethylformamide or N-methylpyrrolidone, preferably in dimethylformamide or N-methylpyrrolidone and very preferably in dimethylformamide.

The reaction temperatures for the conversion are between 0° C. and the boiling point of the solvent used. The conversion is preferably carried out at temperatures between 15 and 40° C., very particularly preferably between 20 and 30° C.

A further aspect of the invention is therefore one of the processes described above for preparing roflumilast, characterized in that reaction of the anion of 4-amino-3,5-dichloro-pyridine (1) with an activated derivative of 3-cyclopropyl-methoxy-4-difluoromethoxybenzoic acid (2) is carried out at a temperature between 0° C. and the boiling point of the inert solvent used, preferably at a temperature between 15 and 40° C. and particularly preferably at a temperature between 20 and 30° C.

In the reaction of the anion of 4-amino-3,5-dichloropyridine (1) with an activated derivative of 3-cyclopropyl-methoxy-4-difluoromethoxybenzoic acid (2) it is possible to add either the anion of 4-amino-3,5-dichloropyridine (1) or the activated derivative of 3-cyclopropylmethoxy-4-difluoromethoxybenzoic acid (2) to the respective other reactant. However, the process in which the activated derivative of 3-cyclopropylmethoxy-4-difluoromethoxybenzoic acid is added as second reactant to the anion of 4-amino-3,5-dichloropyridine (1) is preferred.

Activated derivatives of 3-cyclopropylmethoxy-4-difluoromethoxybenzoic acid (2) may be, for example, the corresponding acid halides, especially the acid chloride or else an anhydride [LG then corresponds to Cl, Br or OC(O)-1-4C-alkyl]. The acid halides are preferred in this connection, and the add chloride is very particularly preferred.

A further aspect of the invention is therefore the process described above for preparing roflumilast, characterized in that the activated derivative of 3-cyclopropylmethoxy-4-difluoromethoxybenzoic acid is a 3-cyclopropylmethoxy-4-difluoromethoxybenzoyl halide, especially 3-cyclopropyl-methoxy-4-difluoromethoxybenzoyl chloride.

Strong bases selected from the group of KOtBu, NaOtBu and LiOtBu are particularly suitable for preparing the anion of 4-amino-3,5-dichloropyridine. The use of KOtBu is preferred.

A further aspect of the invention is therefore one of the processes described above for preparing roflumilast, characterized in that a base selected from the group of KOtBu, NaOtBu or LiOtBu is used to prepare the anion of 4-amino-3,5-dichloropyridine. KOtBu is preferably used.

The molar ratio of employed base to 4-amino-,3,5-dichloropyridine is in this case advantageously in the range from 0.8 to 1.1 and preferably in the range from 0.9 to 1.0.

A further aspect of the invention is therefore one of the processes described above for preparing roflumilast characterized in that the molar ratio of employed base to 4-amino-3,5-dichloropyridine in the anion formation is between 0.8 and 1.1, preferably between 0.9 and 1.0.

The activated derivative of 3-cyclopropylmethoxy-4-difluoromethoxybenzoic acid is prepared by methods known to the skilled person.

The corresponding acid chloride is, for example, preferably prepared by reacting 3-cyclopropylmethoxy-4-difluoromethoxybenzoic acid with thionyl chloride in the presence of catalytic amounts of dimethylformamide in an inert solvent. An example of an inert solvent is toluene or xylene; the chlorination reaction is typically carried out at 70 to 90° C.

The roflumilast prepared by the processes described above is distinguished by a purity of $\geqq$99% by weight. Crystallization from isopropanol/water (ratio: between 85:15 and 100:0% by volume, preferably between 90:10 and 95:5% by volume) allows the purity to be increased further to $\geqq$99.8% by weight.

A further aspect of the invention is therefore one of the processes described above for preparing roflumilast, characterized in that the product resulting from the process is recrystallized in a mixture of isopropanol and water (ratio isopropanol/water: between 85:15 and 100:0% by volume, preferably between 90:10 and 95:5% by volume).

Further aspects of the invention which should be mentioned are:

Roflumilast prepared by one of the processes described above, characterized in that its purity is $\geqq$99% by weight, preferably $\geqq$99.8% by weight.

Roflumilast prepared by one of the processes described above, characterized in that it contains less than 0.1% by weight, preferably 0.05% by weight, of the by-product N-(3,5-dichloropyrid-4-yl)-3-cyclopropylmethoxy-4-hydroxy-benzamide.

The processes according to the invention for the preparation of roflumilast are in particular useful for the large-scale preparation of roflumilast; high-purity roflumilast can be prepared in a scale of about 5 to 500 kg per batch.

Roflumilast prepared by one of the processes described above can be used in human and veterinary medicine for the treatment and prophylaxis, for example, of the following diseases: acute and chronic (especially inflammatory and allergen-induced) airway disorders of various etiologies (bronchitis, allergic bronchitis, bronchial asthma, emphysema, COPD); dermatoses (especially of a proliferative, inflammatory and allergic nature) such as, for example, psoriasis (vulgaris), toxic and allergic contact eczema, atopic eczema, seborrhoic eczema, lichen simplex, sunburn, pruritus in the genitoanal region, alopecia areata, hypertrophic scars, discoid lupus erythematosus, follicular and extensive pyodermas, endogenous and exogenous acne, acne rosacea and other proliferative, inflammatory and allergic skin disorders; disorders based on excessive release of TNF an leukotrienes, e.g. disorders of the arthritic type (rheumatoid arthritis, rheumatoid spondylitis, osteoarthritis and other arthritic states), disorders of the immune system (AIDS, multiple sclerosis), types of shock [septic shock, endotoxin shock, gram-negative sepsis, toxic shock syndrome and ARDS (adult respiratory distress syndrome)] and generalized inflammations in the gastrointestinal region (Crohn's disease and ulcerative colitis); disorders based on allergic and/or chronic abnormal immunological reactions in the region of the upper airways (pharyngeal space, nose) and adjacent regions (paranasal sinuses, eyes), such as, for example, allergic rhinitis/sinusitis, chronic rhinitis/sinusitis, allergic conjunctivitis and nasal polyps; but also cardiac disorders which can be treated by PDE inhibitors, such as, for example, heart failure, or disorders which can be treated owing to the tissue-relaxant effect of PDE inhibitors, such as, for example, erectile dysfunction or colic of the kidneys and ureters connected with kidney stones, or else disorders of the CNS such as, for example, depressions or arteriosclerotic dementia.

The invention therefore further relates to roflumilast prepared by one of the processes described above for use in the treatment and/or prophylaxis of diseases, especially the diseases mentioned.

The invention also relates to the use of roflumilast prepared by one of the processes described above for the production of pharmaceutical compositions which are employed for the treatment and/or prophylaxis of the diseases mentioned. The disease is preferably an acute or chronic airway disorder (for example asthma, bronchitis, allergic rhinitis, emphysema and COPD), a dermatosis or an arthritic disorder (for example rheumatoid arthritis, rheumatoid spondylitis and osteoarthritis).

The invention furthermore relates to a method for the treatment of mammals, including humans, suffering from one of the mentioned diseases. The method is characterized in that a therapeutically effective amount of roflumilast prepared by one of the processes described above is administered together with conventional auxiliaries and/or excipients to the mammal with the disease. Preferably the disease is an acute or chronic airway disorder (for example asthma, bronchitis, allergic rhinits, emphysema and COPD), a dermatosis or an arthritic disorder (for example rheumatoid arthritis, rheumatoid spondylitis and osteoarthritis).

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

The pharmaceutical compositions are prepared by processes, which are known per se and familiar to the person skilled in the art. As pharmaceutical composition, the roflumilast prepared according to one of the above-mentioned processes is either employed as such, or preferably in combination with suitable pharmaceutical auxiliaries and/or excipients, e.g. in the form of tablets, coated tablets, capsules, caplets, suppositories, emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved. In the international patent application WO03/070279 oral dosage forms comprising roflumilast are described.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

For the treatment of disorders of the respiratory tract, the roflumilast prepared according to one of the above-mentioned processes is preferably also administered by inhalation in the form of an aerosol; the aerosol particles of solid, liquid or mixed composition preferably having a diameter of 0.5 to 10 μm, advantageously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the roflumilast prepared according to one of the above-mentioned processes is in particular administered in the form of those pharmaceutical compositions, which are suitable for topical application. For the production of the pharmaceutical compositions, the roflumilast prepared according to one of the above-mentioned processes is preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions. In the international patent application WO03/099334 topically applicable pharmaceutical preparations comprising roflumilast are described.

The dosage of the roflumilast prepared according to one of the above-mentioned processes is in the order of magnitude customary for PDE inhibitors, it being possible to administer the daily dose in one or more dosage units. Customary dosages are disclosed for example in WO 95/01338. In general, oral dosage forms contain from 0.01 mg to 5 mg, preferably from 0.05 mg to 2.5 mg, particularly preferably 0.1 mg to 0.5 mg of roflumilast per dosage unit. Dosage forms for topical administration contain from 0.005 mg to 5 mg, preferably 0.01 mg to 2.5 mg particularly preferably 0.1 mg to 0.5 mg of roflumilast per dosage unit. Typically, pharmaceutical compositions of the invention contain 0.01 mg, 0.1 mg, 0.125 mg, 0.25 mg or 0.5 mg of roflumilast per dosage unit.

The following examples serve to illustrate the invention further without restricting It.

Synthesis of Roflumilast—Coupling Step

The potassium salt suspension of the anion of 4-amino-3,5-dichloropyridine in DMF (2-2.5 equivalents) is introduced into a reaction vessel. A solution of 3-cyclopropylmethoxy-4-difluoromethoxybenzoyl chloride (1 equivalent) in DMF is slowly added to this suspension while stirring vigorously at a temperature of 15 to 40° C., preferably 20 to 30° C. After the reaction is complete, water is slowly added while stirring at 15-25° C., and the pH is adjusted to 2-3 with hydrochloric acid.

The solid is centrifuged or filtered, washed with water, resuspended in a sodium hydroxide solution (pH=9-10), centrifuged or filtered again and washed with water. This moist crude material is, if desired, subjected to a recrystallization from an isopropanol/water mixture (ratio between 85:15 and 100:0, preferably 95:5% by volume). The resulting product is centrifuged or filtered and dried in vacuo at a temperature not exceeding 60° C.

Synthesis of 3-cyclopropylmethoxy-4-difluoromethoxybenzoyl chloride

A reaction vessel is charged with toluene, a catalytic amount of DMF (1-5% by weight of the amount of thionyl chloride employed) and 1 equivalent of 3-cyclopropylmethoxy-4-difluoromethoxybenzoic acid. While stirring, 1 to 4 equivalents of thionyl chloride are slowly added at 70 to 90° C.

After the reaction is complete, the reaction mixture is concentrated in vacuo at 45 to 60° C., and the solvent toluene is replaced by DMF; the resulting 3-cyclopropylmethoxy-4-difluoromethoxybenzoyl chloride solution is used without further purification in the subsequent coupling step.

Synthesis of the potassium salt of 4-amino-3,5-dichloropyridine

A reaction vessel is charged with DMF and 4-amino-3,5-dichloropyridine (1 equivalent). While stirring vigorously, potassium tert-butoxide (0.8-1.1, preferably 0.9-1.0 equivalent) is added in portions at a temperature between 15 and 30° C. A suspension of the potassium salt of the anion of 4-amino-3,5-dichloropyridine is obtained and is employed without further purification for the subsequent coupling step.

Process A: Standard process as described above; synthesis of the potassium salt of 4-amino-3,5-dichloropyridine using 1 equivalent of 4-amino-3,5-dichloropyridine and 1 equivalent of potassium tert-butoxide.

Process B: Differing from process A in that the potassium salt of 4-amino-3,5-dichloropyridine is prepared using 1 equivalent of 4-amino-3,5-dichloropyridine and 0.91 equivalent of potassium tert-butoxide.

Process C: Differing from the standard process in that N-methylpyrrolidone is used as solvent instead of DMF in the coupling step and in the preparation of the potassium salt of 4-amino-3,5-dichloropyridine.

Process D: Differing from the standard process in that only 1.8 equivalents, instead of 2-2.5 equivalents, of the potassium salt of 4-amino-3,5-dichloropyridine are employed in the coupling step.

Process E Differing from the standard process in that 2.7 equivalents, instead of 2-2.5 equivalents, of the potassium salt of 4-amino-3,5-dichloropyridine are employed in the coupling step.

Process F: Differing from the standard process in that the potassium salt of 4-amino-3,5-dichloropyridine is prepared using 1 equivalent of 4-amino-3,5-dichloropyridine and 1.83 equivalents of potassium tert-butoxide.

Process G: The Improved process described in Organic Process Research & Development 2, 157-168 (1998) for preparing piclamilast (coupling step) is applied analogously to the preparation of roflumilast.

| Process | Purity after recrystallization from isopropanol/water (data in % by weight) | Content of by-product N-(3,5-dichloropyrid-4-yl)-3-cyclopropylmethoxy-4-hydroxy-benzamide (data in % by weight) |
| --- | --- | --- |
| A | ≧99.8 | <0.05 |
| B | ≧99.8 | <0.05 |
| C | ≧99.8 | <0.05 |
| D | ≧99.8 | <0.05 |
| E | ≧99.8 | <0.05 |
| F | 96.2 | 0.8 |
| G | 95.4 | 3.47 |

The invention claimed is:

1. A process for the preparation of roflumilast by reacting an anion of 4-amino-3,5-dichloropyridine (1)

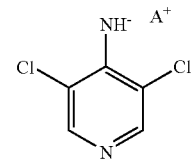

(1)

in which A$^+$ is a potassium cation, with an activated derivative of 3-cyclopropylmethoxy-4-difluoromethoxybenzoic acid (2),

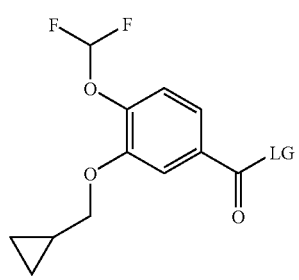

(2)

in which LG is a suitable leaving group selected from a chlorine atom, a bromine atom or a radical of the formula OC(O)-1-4C-alkyl, wherein
  (a) the molar ratio of the employed anion of 4-amino-3,5-dichloropyridine (1) to the activated derivative of 3-cyclopropylmethoxy-4-difluoromethoxybenzoic acid (2) is at least 1.8 and at most 2.7,
  (b) the reaction of the anion of 4-amino-3,5-dichloropyridine (1) with the activated derivative of 3-cyclopropylmethoxy-4-difluoromethoxybenzoic acid (2) is carried out in a solvent selected from dimethylformamide or N-methylpyrrolidone, (c) the reaction of the anion of 4-amino-3,5-dichloropyridine (1) with the activated derivative of 3-cyclopropylmethoxy-4-difluoromethoxybenzoic acid (2) is carried out at a temperature between 0° C. and the boiling point of the solvent used, and (d) KOtBu is used to prepare the anion of 4-amino-3,5-dichloropyridine (1).

2. The process according to claim 1, wherein the molar ratio of the employed anion of 4-amino-3,5-dichloropyridine (1) to the activated derivative of 3-cyclopropylmethoxy-4-difluoromethoxybenzoic acid (2) is at least 2 and at most 2.5.

3. The process according to claim 1, wherein the molar ratio of the employed anion of 4-amino-3,5-dichloropyridine (1) to the activated derivative of 3-cyclopropylmethoxy-4-difluoromethoxybenzoic acid (2) is 2.2.

4. The process according to claim 1, wherein the reaction of the anion of 4-amino-3,5-dichloropyridine (1) with an activated derivative of 3-cyclopropylmethoxy-4-difluoromethoxybenzoic acid (2) is carried out in dimethylformamide.

5. The process according to claim 1, wherein the reaction of the anion of 4-amino-3,5-dichloropyridine (1) with an activated derivative of 3-cyclopropylmethoxy-4-difluoromethoxybenzoic acid (2) is carried out in N-methylpyrrolidone.

6. The process according to claim 1, wherein the reaction of the anion of 4-amino-3,5-dichloropyridine (1) with an activated derivative of 3-cyclopropylmethoxy-4-difluoromethoxybenzoic acid (2) is carried out at a temperature between 15° C. and 40° C.

7. The process according to claim 4, wherein the reaction of the anion of 4-amino-3,5-dichloropyridine (1) with an activated derivative of 3-cyclopropylmethoxy-4-difluoromethoxybenzoic acid (2) is carried out at a temperature between 15° C. and 40° C.

8. The process according to claim 5, wherein the reaction of the anion of 4-amino-3,5-dichloropyridine (1) with an activated derivative of 3-cyclopropylmethoxy-4-difluoromethoxybenzoic acid (2) is carried out at a temperature between 15° C.and 40° C.

9. The process according to claim 1, wherein the reaction of the anion of 4-amino-3,5-dichloropyridine (1) with an activated derivative of 3-cyclopropylmethoxy-4-difluoromethoxybenzoic acid (2) is carried out at a temperature between 20° C. and 30° C.

10. The process according to claim 4, wherein the reaction of the anion of 4-amino-3,5-dichloropyridine (1) with an activated derivative of 3-cyclopropylmethoxy-4-difluoromethoxybenzoic acid (2) is carried out at a temperature between 20° C. and 30° C.

11. The process according to claim 5, wherein the reaction of the anion of 4-amino-3,5-dichloropyridine (1) with an activated derivative of 3-cyclopropylmethoxy-4-difluoromethoxybenzoic acid (2) is carried out at a temperature between 20° C. and 30° C.

12. The process according to claim 1, wherein the activated derivative of 3-cyclopropylmethoxy-4-difluoromethoxybenzoic acid (2) is 3-cyclopropylmethoxy-4-difluoromethoxybenzoyl chloride.

13. The process according to claim 4, wherein the activated derivative of 3-cyclopropylmethoxy-4-difluoromethoxybenzoic acid (2) is 3-cyclopropylmethoxy-4-difluoromethoxybenzoyl chloride.

14. The process according to claim 5, wherein the activated derivative of 3-cyclopropylmethoxy-4-difluoromethoxybenzoic acid (2) is 3-cyclopropylmethoxy-4-difluoromethoxybenzoyl chloride.

15. The process according to claim 6, wherein the activated derivative of 3-cyclopropylmethoxy-4-difluoromethoxybenzoic acid (2) is 3-cyclopropylmethoxy-4-difluoromethoxybenzoyl chloride.

16. The process according to claim 7, wherein the activated derivative of 3-cyclopropylmethoxy-4-difluoromethoxybenzoic acid (2) is 3-cyclopropylmethoxy-4-difluoromethoxybenzoyl chloride.

17. The process according to claim 8, wherein the activated derivative of 3-cyclopropylmethoxy-4-difluoromethoxybenzoic acid (2) is 3-cyclopropylmethoxy-4-difluoromethoxybenzoyl chloride.

18. The process according to claim 9, wherein the activated derivative of 3-cyclopropylmethoxy-4-difluoromethoxybenzoic acid (2) is 3-cyclopropylmethoxy-4-difluoromethoxybenzoyl chloride.

19. The process according to claim 10, wherein the activated derivative of 3-cyclopropylmethoxy-4-difluoromethoxybenzoic acid (2) is 3-cyclopropylmethoxy-4-difluoromethoxybenzoyl chloride.

20. The process according to claim 11, wherein the activated derivative of 3-cyclopropylmethoxy-4-difluoromethoxybenzoic acid (2) is 3-cyclopropylmethoxy-4-difluoromethoxybenzoyl chloride.

21. The process according to claim 1, wherein the activated derivative of 3-cyclopropylmethoxy-4-difluoromethoxybenzoic acid (2) is 3-cyclopropylmethoxy-4-difluoromethoxybenzoyl bromide.

22. The process according to claim 4, wherein the activated derivative of 3-cyclopropylmethoxy-4-difluoromethoxybenzoic acid (2) is 3-cyclopropylmethoxy-4-difluoromethoxybenzoyl bromide.

23. The process according to claim 5, wherein the activated derivative of 3-cyclopropylmethoxy-4-difluoromethoxybenzoic acid (2) is 3-cyclopropylmethoxy-4-difluoromethoxybenzoyl bromide.

24. The process according to claim 6, wherein the activated derivative of 3-cyclopropylmethoxy-4-difluoromethoxybenzoic acid (2) is 3-cyclopropylmethoxy-4-difluoromethoxybenzoyl bromide.

25. The process according to claim 7, wherein the activated derivative of 3-cyclopropylmethoxy-4-difluoromethoxybenzoic acid (2) is 3-cyclopropylmethoxy-4-difluoromethoxybenzoyl bromide.

26. The process according to claim 8, wherein the activated derivative of 3-cyclopropylmethoxy-4-difluoromethoxybenzoic acid (2) is 3-cyclopropylmethoxy-4-difluoromethoxybenzoyl bromide.

27. The process according to claim 9, wherein the activated derivative of 3-cyclopropylmethoxy-4-difluoromethoxybenzoic acid (2) is 3-cyclopropylmethoxy-4-difluoromethoxybenzoyl bromide.

28. The process according to claim 10, wherein the activated derivative of 3-cyclopropylmethoxy-4-difluoromethoxybenzoic acid (2) is 3-cyclopropylmethoxy-4-difluoromethoxybenzoyl bromide.

29. The process according to claim 11, wherein the activated derivative of 3-cyclopropylmethoxy-4-difluoromethoxybenzoic acid (2) is 3-cyclopropylmethoxy-4-difluoromethoxybenzoyl bromide.

30. The process according to claim 1, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

31. The process according to claim 4, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

32. The process according to claim 5, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

33. The process according to claim 6, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

34. The process according to claim 7, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

35. The process according to claim 8, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

36. The process according to claim 9, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

37. The process according to claim 10, wherein the activated derivative of 3-cyclopropylmethoxy-4-difluoromethoxybenzoic acid (2) is a 3-cyclopropylmethoxy-4-difluoromethoxybenzoic acid 1-40C-alkyl-ester.

38. The process according to claim 11, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

39. The process according to claim 13, further comprising the step of recrystallizing the roflumilast in a mixture of isopropanol and water wherein the ratio of isopropanol/water is between 85:15 and 100:0% by volume.

40. The process according to claim 14, further comprising the step of recrystallizing the roflumilast in a mixture of isopropanol and water wherein the ratio of isopropanol/water is between 85:15 and 100:0% by volume.

41. The process according to claim 16, further comprising the step of recrystallizing the roflumilast in a mixture of isopropanol and water wherein the ratio of isopropanol/water is between 85:15 and 100:0% by volume.

42. The process according to claim 17, further comprising the step of recrystallizing the roflumilast in a mixture of isopropanol and water wherein the ratio of isopropanol/water is between 85:15 and 100:0% by volume.

43. The process according to claim 19, further comprising the step of recrystallizing the roflumilast in a mixture of isopropanol and water wherein the ratio of isopropanol/water is between 85:15 and 100:0% by volume.

44. The process according to claim 20, further comprising the step of recrystallizing the roflumilast in a mixture of isopropanol and water wherein the ratio of isopropanol/water is between 85:15 and 100:0% by volume.

45. The process according to claim 22, further comprising the step of recrystallizing the roflumilast in a mixture of isopropanol and water wherein the ratio of isopropanol/water is between 85:15 and 100:0% by volume.

46. The process according to claim 23, further comprising the step of recrystallizing the roflumilast in a mixture of isopropanol and water wherein the ratio of isopropanol/water is between 85:15 and 100:0% by volume.

47. The process according to claim 25, further comprising the step of recrystallizing the roflumilast in a mixture of isopropanol and water wherein the ratio of isopropanol/water is between 85:15 and 100:0% by volume.

48. The process according to claim 26, further comprising the step of recrystallizing the roflumilast in a mixture of isopropanol and water wherein the ratio of isopropanol/water is between 85:15 and 100:0% by volume.

49. The process according to claim 28, further comprising the step of recrystallizing the roflumilast in a mixture of isopropanol and water wherein the ratio of isopropanol/water is between 85:15 and 100:0% by volume.

50. The process according to claim 29, further comprising the step of recrystallizing the roflumilast in a mixture of isopropanol and water wherein the ratio of isopropanol/water is between 85:15 and 100:0% by volume.

51. The process according to claim 31, further comprising the step of recrystallizing the roflumilast in a mixture of isopropanol and water wherein the ratio of isopropanol/water is between 85:15 and 100:0% by volume.

52. The process according to claim 32, further comprising the step of recrystallizing the roflumilast in a mixture of isopropanol and water wherein the ratio of isopropanol/water is between 85:15 and 100:0% by volume.

53. The process according to claim 34, further comprising the step of recrystallizing the roflumilast in a mixture of isopropanol and water wherein the ratio of isopropanol/water is between 85:15 and 100:0% by volume.

54. The process according to claim 35, further comprising the step of recrystallizing the roflumilast in a mixture of isopropanol and water wherein the ratio of isopropanol/water is between 85:15 and 100:0% by volume.

55. The process according to claim 37, further comprising the step of recrystallizing the roflumilast in a mixture of isopropanol and water wherein the ratio of isopropanol/water is between 85:15 and 100:0% by volume.

56. The process according to claim 38, further comprising the step of recrystallizing the roflumilast in a mixture of isopropanol and water wherein the ratio of isopropanol/water is between 85:15 and 100:0% by volume.

57. The process according to claim 2, wherein the reaction of the anion of 4-amino-3,5-dichloropyridine (1) with an activated derivative of 3-cyclopropylmethoxy-4-difluoromethoxybenzoic acid (2) is carried out in dimethylformamide.

58. The process according to claim 2, wherein the reaction of the anion of 4-amino-3,5-dichloropyridine (1) with an activated derivative of 3-cyclopropylmethoxy-4-difluoromethoxybenzoic acid (2) is carried out in N-methylpyrrolidone.

59. The process according to claim 2, wherein the reaction of the anion of 4-amino-3,5-dichloropyridine (1) with an activated derivative of 3-cyclopropylmethoxy-4-difluoromethoxybenzoic acid (2) is carried out at a temperature between 15° C. and 40° C.

60. The process according to claim 57, wherein the reaction of the anion of 4-amino-3,5-dichloropyridine (1) with an activated derivative of 3-cyclopropylmethoxy-4-difluoromethoxybenzoic acid (2) is carried out at a temperature between 15° C. and 40° C.

61. The process according to claim 58, wherein the reaction of the anion of 4-amino-3,5-dichloropyridine (1) with an activated derivative of 3-cyclopropylmethoxy-4-difluoromethoxybenzoic acid (2) is carried out at a temperature between 15° C. and 40° C.

62. The process according to claim 2, wherein the reaction of the anion of 4-amino-3,5-dichloropyridine (1) with an activated derivative of 3-cyclopropylmethoxy-4-difluoromethoxybenzoic acid (2) is carried out at a temperature between 20° C. and 30° C.

63. The process according to claim 57, wherein the reaction of the anion of 4-amino-3,5-dichloropyridine (1) with an activated derivative of 3-cyclopropylmethoxy-4-difluoromethoxybenzoic acid (2) is carried out at a temperature between 20° C. and 30° C.

64. The process according to claim 58, wherein the reaction of the anion of 4-amino-3,5-dichloropyridine (1) with an activated derivative of 3-cyclopropylmethoxy-4-difluoromethoxybenzoic acid (2) is carried out at a temperature between 20° C. and 30° C.

65. The process according to claim 2, wherein the activated derivative of 3-cyclopropylmethoxy-4-difluoromethoxybenzoic acid (2) is 3-cyclopropylmethoxy-4-difluoromethoxybenzoyl chloride.

66. The process according to claim 57, wherein the activated derivative of 3-cyclopropylmethoxy-4-difluoromethoxybenzoic acid (2) is 3-cyclopropylmethoxy-4-difluoromethoxybenzoyl chloride.

67. The process according to claim 58, wherein the activated derivative of 3-cyclopropylmethoxy-4-difluoromethoxybenzoic acid (2) is 3-cyclopropylmethoxy-4-difluoromethoxybenzoyl chloride.

68. The process according to claim 59, wherein the activated derivative of 3-cyclopropylmethoxy-4-difluoromethoxybenzoic acid (2) is 3-cyclopropylmethoxy-4-difluoromethoxybenzoyl chloride.

69. The process according to claim 60, wherein the activated derivative of 3-cyclopropylmethoxy-4-difluoromethoxybenzoic acid (2) is 3-cyclopropylmethoxy-4-difluoromethoxybenzoyl chloride.

70. The process according to claim 61, wherein the activated derivative of 3-cyclopropylmethoxy-4-difluoromethoxybenzoic acid (2) is 3-cyclopropylmethoxy-4-difluoromethoxybenzoyl chloride.

71. The process according to claim 62, wherein the activated derivative of 3-cyclopropylmethoxy-4-difluoromethoxybenzoic acid (2) is 3-cyclopropylmethoxy-4-difluoromethoxybenzoyl chloride.

72. The process according to claim 63, wherein the activated derivative of 3-cyclopropylmethoxy-4-difluoromethoxybenzoic acid (2) is 3-cyclopropylmethoxy-4-difluoromethoxybenzoyl chloride.

73. The process according to claim 64, wherein the activated derivative of 3-cyclopropylmethoxy-4-difluoromethoxybenzoic acid (2) is 3-cyclopropylmethoxy-4-difluoromethoxybenzoyl chloride.

74. The process according to claim 2, wherein the activated derivative of 3-cyclopropylmethoxy-4-difluoromethoxybenzoic acid (2)is 3 -cyclopropylmethoxy-4-difluoromethoxybenzoyl bromide.

75. The process according to claim 57, wherein the activated derivative of 3-cyclopropylmethoxy-4-difluoromethoxybenzoic acid (2) is 3-cyclopropylmethoxy-4-difluoromethoxybenzoyl bromide.

76. The process according to claim 58, wherein the activated derivative of 3-cyclopropylmethoxy-4-difluoromethoxybenzoic acid (2) is 3-cyclopropylmethoxy-4-difluoromethoxybenzoyl bromide.

77. The process according to claim 59, wherein the activated derivative of 3-cyclopropylmethoxy-4-difluoromethoxybenzoic acid (2) is 3-cyclopropylmethoxy-4-difluoromethoxybenzoyl bromide.

78. The process according to claim 60, wherein the activated derivative of 3-cyclopropylmethoxy-4-difluoromethoxybenzoic acid (2) is 3-cyclopropylmethoxy-4-difluoromethoxybenzoyl bromide.

79. The process according to claim 61, wherein the activated derivative of 3-cyclopropylmethoxy-4-difluoromethoxybenzoic acid (2) is 3-cyclopropylmethoxy-4-difluoromethoxybenzoyl bromide.

80. The process according to claim 62, wherein the activated derivative of 3-cyclopropylmethoxy-4-difluoromethoxybenzoic acid (2) is 3-cyclopropylmethoxy-4-difluoromethoxybenzoyl bromide.

81. The process according to claim 63, wherein the activated derivative of 3-cyclopropylmethoxy-4-difluoromethoxybenzoic acid (2) is 3-cyclopropylmethoxy-4-difluoromethoxybenzoyl bromide.

82. The process according to claim 64, wherein the activated derivative of 3-cyclopropylmethoxy-4-difluoromethoxybenzoic acid (2) is 3-cyclopropylmethoxy-4-difluoromethoxybenzoyl bromide.

83. The process according to claim 2, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

84. The process according to claim 57, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

85. The process according to claim 58, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

86. The process according to claim 59, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

87. The process according to claim 60, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

88. The process according to claim 61, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

89. The process according to claim 62, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

90. The process according to claim 63, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

91. The process according to claim 64, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

92. The process according to claim 66, further comprising the step of recrystallizing the roflumilast in a mixture of isopropanol and water wherein the ratio of isopropanol/water is between 85:15 and 100:0% by volume.

93. The process according to claim 67, further comprising the step of recrystallizing the roflumilast in a mixture of isopropanol and water wherein the ratio of isopropanol/water is between 85:15 and 100:0% by volume.

94. The process according to claim 69, further comprising the step of recrystallizing the roflumilast in a mixture of isopropanol and water wherein the ratio of isopropanol/water is between 85:15 and 100:0% by volume.

95. The process according to claim 70, further comprising the step of recrystallizing the roflumilast in a mixture of isopropanol and water wherein the ratio of isopropanol/water is between 85:15 and 100:0% by volume.

96. The process according to claim 72, further comprising the step of recrystallizing the roflumilast in a mixture of isopropanol and water wherein the ratio of isopropanol/water is between 85:15 and 100:0% by volume.

97. The process according to claim 73, further comprising the step of recrystallizing the roflumilast in a mixture of isopropanol and water wherein the ratio of isopropanol/water is between 85:15 and 100:0% by volume.

98. The process according to claim 75, further comprising the step of recrystallizing the roflumilast in a mixture of isopropanol and water wherein the ratio of isopropanol/water is between 85:15 and 100:0% by volume.

99. The process according to claim 76, further comprising the step of recrystallizing the roflumilast in a mixture of isopropanol and water wherein the ratio of isopropanol/water is between 85:15 and 100:0% by volume.

100. The process according to claim 78, further comprising the step of recrystallizing the roflumilast in a mixture of isopropanol and water wherein the ratio of isopropanol/water is between 85:15 and 100:0% by volume.

101. The process according to claim 79, further comprising the step of recrystallizing the roflumilast in a mixture of isopropanol and water wherein the ratio of isopropanol/water is between 85:15 and 100:0% by volume.

102. The process according to claim 81, further comprising the step of recrystallizing the roflumilast in a mixture of isopropanol and water wherein the ratio of isopropanol/water is between 85:15 and 100:0% by volume.

103. The process according to claim 82, further comprising the step of recrystallizing the roflumilast in a mixture of isopropanol and water wherein the ratio of isopropanol/water is between 85:15 and 100:0% by volume.

104. The process according to claim 84, further comprising the step of recrystallizing the roflumilast in a mixture of isopropanol and water wherein the ratio of isopropanol/water is between 85:15 and 100:0% by volume.

105. The process according to claim 85, further comprising the step of recrystallizing the roflumilast in a mixture of isopropanol and water wherein the ratio of isopropanol/water is between 85:15 and 100:0% by volume.

106. The process according to claim 87, further comprising the step of recrystallizing the roflumilast in a mixture of isopropanol and water wherein the ratio of isopropanol/water is between 85:15 and 100:0% by volume.

107. The process according to claim 88, further comprising the step of recrystallizing the roflumilast in a mixture of isopropanol and water wherein the ratio of isopropanol/water is between 85:15 and 100:0% by volume.

108. The process according to claim 90, further comprising the step of recrystallizing the roflumilast in a mixture of isopropanol and water wherein the ratio of isopropanol/water is between 85:15 and 100:0% by volume.

109. The process according to claim 91, further comprising the step of recrystallizing the roflumilast in a mixture of isopropanol and water wherein the ratio of isopropanol/water is between 85:15 and 100:0% by volume.

110. The process according to claim 3, wherein the reaction of the anion of 4-amino-3,5-dichloropyridine (1) with an activated derivative of 3-cyclopropylmethoxy-4-difluoromethoxybenzoic acid (2) is carried out in dimethylformamide.

111. The process according to claim 3, wherein the reaction of the anion of 4-amino-3,5-dichloropyridine (1) with an activated derivative of 3-cyclopropylmethoxy-4-difluoromethoxybenzoic acid (2) is carried out in N-methylpyrrolidone.

112. The process according to claim 3, wherein the reaction of the anion of 4-amino-3,5-dichloropyridine (1) with an activated derivative of 3-cyclopropylmethoxy-4-difluoromethoxybenzoic acid (2) is carried out at a temperature between 15° C. and 40° C.

113. The process according to claim 110, wherein the reaction of the anion of 4-amino-3,5-dichloropyridine (1) with an activated derivative of 3-cyclopropylmethoxy-4-difluoromethoxybenzoic acid (2) is carried out at a temperature between 15° C. and 40° C.

114. The process according to claim 111, wherein the reaction of the anion of 4-amino-3,5-dichloropyridine (1) with an activated derivative of 3-cyclopropylmethoxy-4-difluoromethoxybenzoic acid (2) is carried out at a temperature between 15° C. and 40° C.

115. The process according to claim 3, wherein the reaction of the anion of 4-amino-3,5-dichloropyridine (1) with an activated derivative of 3-cyclopropylmethoxy-4-difluoromethoxybenzoic acid (2) is carried out at a temperature between 20° C. and 30° C.

116. The process according to claim 110, wherein the reaction of the anion of 4-amino-3,5-dichloropyridine (1) with an activated derivative of 3-cyclopropylmethoxy-4-difluoromethoxybenzoic acid (2) is carried out at a temperature between 20° C. and 30° C.

117. The process according to claim 111, wherein the reaction of the anion of 4-amino-3,5-dichloropyridine (1) with an activated derivative of 3-cyclopropylmethoxy-4-difluoromethoxybenzoic acid (2) is carried out at a temperature between 20° C. and 30° C.

118. The process according to claim 3, wherein the activated derivative of 3-cyclopropylmethoxy-4-difluoromethoxybenzoic acid (2) is 3-cyclopropylmethoxy-4-difluoromethoxybenzoyl chloride.

119. The process according to claim 110, wherein the activated derivative of 3-cyclopropylmethoxy-4-difluoromethoxybenzoic acid (2) is 3-cyclopropylmethoxy-4-difluoromethoxybenzoyl chloride.

120. The process according to claim 111, wherein the activated derivative of 3-cyclopropylmethoxy-4-difluoromethoxybenzoic acid (2) is 3-cyclopropylmethoxy-4-difluoromethoxybenzoyl chloride.

121. The process according to claim 112, wherein the activated derivative of 3-cyclopropylmethoxy-4-difluoromethoxybenzoic acid (2) is 3-cyclopropylmethoxy-4-difluoromethoxybenzoyl chloride.

122. The process according to claim 113, wherein the activated derivative of 3-cyclopropylmethoxy-4-difluoromethoxybenzoic acid (2) is 3-cyclopropylmethoxy-4-difluoromethoxybenzoyl chloride.

123. The process according to claim 114, wherein the activated derivative of 3-cyclopropylmethoxy-4-difluoromethoxybenzoic acid (2) is 3-cyclopropylmethoxy-4-difluoromethoxybenzoyl chloride.

124. The process according to claim 115, wherein the activated derivative of 3-cyclopropylmethoxy-4-difluoromethoxybenzoic acid (2) is 3-cyclopropylmethoxy-4-difluoromethoxybenzoyl chloride.

125. The process according to claim 116, wherein the activated derivative of 3-cyclopropylmethoxy-4-difluoromethoxybenzoic acid (2) is 3-cyclopropylmethoxy-4-difluoromethoxybenzoyl chloride.

126. The process according to claim 117, wherein the activated derivative of 3-cyclopropylmethoxy-4-difluoro-

127. The process according to claim 3, wherein the activated derivative of 3-cyclopropylmethoxy-4-difluoromethoxybenzoic acid (2) is 3-cyclopropylmethoxy-4-difluoromethoxybenzoyl bromide.

128. The process according to claim 110, wherein the activated derivative of 3-cyclopropylmethoxy-4-difluoromethoxybenzoic acid (2) is 3-cyclopropylmethoxy-4-difluoromethoxybenzoyl bromide.

129. The process according to claim 111, wherein the activated derivative of 3-cyclopropylmethoxy-4-difluoromethoxybenzoic acid (2) is 3-cyclopropylmethoxy-4-difluoromethoxybenzoyl bromide.

130. The process according to claim 112, wherein the activated derivative of 3-cyclopropylmethoxy-4-difluoromethoxybenzoic acid (2) is 3-cyclopropylmethoxy-4-difluoromethoxybenzoyl bromide.

131. The process according to claim 113, wherein the activated derivative of 3-cyclopropylmethoxy-4-difluoromethoxybenzoic acid (2) is 3-cyclopropylmethoxy-4-difluoromethoxybenzoyl bromide.

132. The process according to claim 114, wherein the activated derivative of 3-cyclopropylmethoxy-4-difluoromethoxybenzoic acid (2) is 3-cyclopropylmethoxy-4-difluoromethoxybenzoyl bromide.

133. The process according to claim 115, wherein the activated derivative of 3-cyclopropylmethoxy-4-difluoromethoxybenzoic acid (2) is 3-cyclopropylmethoxy-4-difluoromethoxybenzoyl bromide.

134. The process according to claim 116, wherein the activated derivative of 3-cyclopropylmethoxy-4-difluoromethoxybenzoic acid (2) is 3-cyclopropylmethoxy-4-difluoromethoxybenzoyl bromide.

135. The process according to claim 117, wherein the activated derivative of 3-cyclopropylmethoxy-4-difluoromethoxybenzoic acid (2) is 3-cyclopropylmethoxy-4-difluoromethoxybenzoyl bromide.

136. The process according to claim 3, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

137. The process according to claim 110, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

138. The process according to claim 111, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

139. The process according to claim 112, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

140. The process according to claim 113, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

141. The process according to claim 114, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

142. The process according to claim 115, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

143. The process according to claim 116, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

144. The process according to claim 117, wherein the activated derivative of 3-cyclopropylmethoxy-4-difluoromethoxybenzoic acid (2) is a 3-cyclopropylmethoxy-4-difluoromethoxybenzoic acid 1-4C-alkyl-ester.

145. The process according to claim 119, further comprising the step of recrystallizing the roflumilast in a mixture of isopropanol and water wherein the ratio of isopropanol/water is between 85:15 and 100:0% by volume.

146. The process according to claim 120, further comprising the step of recrystallizing the roflumilast in a mixture of isopropanol and water wherein the ratio of isopropanol/water is between 85:15 and 100:0% by volume.

147. The process according to claim 122, further comprising the step of recrystallizing the roflumilast in a mixture of isopropanol and water wherein the ratio of isopropanol/water is between 85:15 and 100:0% by volume.

148. The process according to claim 123, further comprising the step of recrystallizing the roflumilast in a mixture of isopropanol and water wherein the ratio of isopropanol/water is between 85:15 and 100:0% by volume.

149. The process according to claim 125, further comprising the step of recrystallizing the roflumilast in a mixture of isopropanol and water wherein the ratio of isopropanol/water is between 85:15 and 100:0% by volume.

150. The process according to claim 126, further comprising the step of recrystallizing the roflumilast in a mixture of isopropanol and water wherein the ratio of isopropanol/water is between 85:15 and 100:0% by volume.

151. The process according to claim 128, further comprising the step of recrystallizing the roflumilast in a mixture of isopropanol and water wherein the ratio of isopropanol/water is between 85:15 and 100:0% by volume.

152. The process according to claim 129, further comprising the step of recrystallizing the roflumilast in a mixture of isopropanol and water wherein the ratio of isopropanol/water is between 85:15 and 100:0% by volume.

153. The process according to claim 131, further comprising the step of recrystallizing the roflumilast in a mixture of isopropanol and water wherein the ratio of isopropanol/water is between 85:15 and 100:0% by volume.

154. The process according to claim 132, further comprising the step of recrystallizing the roflumilast in a mixture of isopropanol and water wherein the ratio of isopropanol/water is between 85:15 and 100:0% by volume.

155. The process according to claim 134, further comprising the step of recrystallizing the roflumilast in a mixture of isopropanol and water wherein the ratio of isopropanol/water is between 85:15 and 100:0% by volume.

156. The process according to claim 135, further comprising the step of recrystallizing the roflumilast in a mixture of isopropanol and water wherein the ratio of isopropanol/water is between 85:15 and 100:0% by volume.

157. The process according to claim 137, further comprising the step of recrystallizing the roflumilast in a mixture of isopropanol and water wherein the ratio of isopropanol/water is between 85:15 and 100:0% by volume.

158. The process according to claim 138, further comprising the step of recrystallizing the roflumilast in a mixture of isopropanol and water wherein the ratio of isopropanol/water is between 85:15 and 100:0% by volume.

159. The process according to claim 140, further comprising the step of recrystallizing the roflumilast in a mixture of isopropanol and water wherein the ratio of isopropanol/water is between 85:15 and 100:0% by volume.

160. The process according to claim 141, further comprising the step of recrystallizing the roflumilast in a mixture of isopropanol and water wherein the ratio of isopropanol/water is between 85:15 and 100:0% by volume.

161. The process according to claim 143, further comprising the step of recrystallizing the roflumilast in a mixture of isopropanol and water wherein the ratio of isopropanol/water is between 85:15 and 100:0% by volume.

162. The process according to claim 144, further comprising the step of recrystallizing the roflumilast in a mixture of isopropanol and water wherein the ratio of isopropanol/water is between 85:15 and 100:0% by volume.

* * * * *